United States Patent
Hengstenberg et al.

(10) Patent No.: US 10,426,907 B2
(45) Date of Patent: Oct. 1, 2019

(54) METHOD AND SYSTEM FOR CONTROLLING A DRUG DOSING DEVICE

(71) Applicant: Drägerwerk AG & Co. KGaA, Lübeck (DE)

(72) Inventors: Andreas Hengstenberg, Reinfeld (DE); Stefan Zimmermann, Burgwedel (DE); Dammon Ziaian, Hannover (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 887 days.

(21) Appl. No.: 14/924,021

(22) Filed: Oct. 27, 2015

(65) Prior Publication Data

US 2016/0114114 A1    Apr. 28, 2016

(30) Foreign Application Priority Data

Oct. 28, 2014  (DE) .................. 10 2014 015 897

(51) Int. Cl.
*A61M 16/18*        (2006.01)
*A61M 16/00*        (2006.01)

(52) U.S. Cl.
CPC ........ *A61M 16/0051* (2013.01); *A61M 16/18* (2013.01); *A61M 2205/502* (2013.01); *A61M 2230/437* (2013.01)

(58) Field of Classification Search
CPC .................. A61M 16/04; A61M 2016/1035
See application file for complete search history.

(56) References Cited

U.S. PATENT DOCUMENTS

| | | | | |
|---|---|---|---|---|
| 6,631,291 B2 * | 10/2003 | Viertio-Oja | .......... | A61B 5/0476 600/544 |
| 2007/0203448 A1 | 8/2007 | Melker et al. | | |
| 2008/0077080 A1 * | 3/2008 | Hengstenberg | ....... | A61M 16/01 604/66 |
| 2012/0277613 A1 * | 11/2012 | Li | .......... | A61B 5/0816 600/532 |
| 2014/0144434 A1 * | 5/2014 | Martin | ................ | A61M 16/104 128/202.22 |
| 2015/0290418 A1 * | 10/2015 | Kaczka | ................ | A61M 16/18 128/200.14 |

FOREIGN PATENT DOCUMENTS

DE    10 2012 203897 A1    9/2013

* cited by examiner

*Primary Examiner* — LaToya M Louis
(74) *Attorney, Agent, or Firm* — McGlew and Tuttle, P.C.

(57) ABSTRACT

A method and a system control a drug dosing device (1) for administering a drug to a patient (19). The quantity (c0) of the drug administered from the drug dosing device (1) is determined or calculated. The concentration of the drug in the gas exhaled by the patient (19) is measured as a first patient value (c1M). A simulation calculation is carried out, in which a second patient value (cp) is calculated from the administered quantity of the drug (I), taking into account a parameter (k10). A simulated first patient value (c1') is calculated in the simulation calculation, taking into account the parameter (k10). A comparison of the simulated first patient value (c1') to the measured first patient value (c1M) is carried out. The parameter (k10) is adapted on the basis of the comparison. The calculated second patient value (cp) is used to generate a control signal (S).

16 Claims, 3 Drawing Sheets

METHOD AND SYSTEM FOR CONTROLLING A DRUG DOSING DEVICE

CROSS REFERENCE TO RELATED APPLICATIONS

This application claims the benefit of priority under 35 U.S.C. § 119 of German Patent Application 10 2014 015 897.7 filed Oct. 28, 2014, the entire contents of which are incorporated herein by reference.

FIELD OF THE INVENTION

The present invention to a method and a system for controlling a drug dosing device.

BACKGROUND OF THE INVENTION

In the field of anesthesia, it has been known for a long time that anesthetics, which may be, for example, propofol, can be administered to the patient intravenously by means of a computer-assisted syringe pump. It is readily possible in this connection to control the syringe pump accurately, so that the quantity, i.e., the rate, of the anesthetic administered to the patient per unit of time can be adjusted accurately. During anesthesia the anesthetic in question is, however, continuously redistributed and broken down in the body of the patient, so that a blood concentration of the anesthetic becomes established, which cannot be easily determined from the quantity administered to the patient. It is known in this connection that this redistribution and breakdown process also has a very different course from patient to patient, even though the actually relevant patient data, such as height, body weight and age are almost in agreement.

Thus, statements can only be made with a very high inaccuracy with respect to the actually present blood concentration of the anesthetic in a specific patient. In addition, the problem arises that up to now it is not technically possible to monitor the propofol concentration in the blood continuously, for example, by means of sensors.

On the other hand, the concentration of the anesthetic in the blood is, however, correlated with the anesthesia and thus with whether or not the desired depth of anesthesia is actually reached. Since this parameter is not directly accessible, it is known from the state of the art to monitor the depth of anesthesia, for example, by means of EEG measurements during an intravenous administration of anesthetic. Depending on the depth of anesthesia determined in this case, the administration of the anesthetic and thus the syringe pump can be controlled.

In addition, it is known, for example, from DE 10 2012 203 897 A1 to describe the redistribution process of the anesthetic in the body of the patient within the framework of a so-called "three-compartment model," wherein it is assumed that an exchange of the anesthetic, which is being administered intravenously, takes place, on the one hand, with the fatty tissue and connective tissue as well as, on the other hand, with the muscles, wherein the course of this exchange has a different rate in each case. In addition, a breakdown takes place at another rate. However, the portion of the anesthetic remaining in the blood circulation, which is not accessible based on measurement, as already explained, is relevant for the anesthesia effect.

It is additionally known from this publication that the rates, with which the anesthetic passes from the blood circulation into both compartments, i.e., the fatty tissue and connection tissue, on the one hand, and muscles, on the other hand, varies widely from patient to patient, which in turn leads to such a model and predictions based thereon to be marked by very great relative errors on the order of magnitude of 30%.

Since, however, the depth of anesthesia depends on the concentration of the anesthetic at the site of action, a control, which is supported alone on such a model, may lead to unnecessary problems. If an excessively high quantity of anesthetic is administered, this may lead to injuries in the patient. On the other hand, an excessively low quantity of anesthetic in the blood circulation may have the result that the patient is not sufficiently deeply anesthetized and possibly perceives parts of the surgical procedure carried out on him, which may in turn result in trauma.

SUMMARY OF THE INVENTION

Therefore, based on the state of the art, an object of the present invention is to provide a method and a system for controlling a drug dosing device, especially a dosing device for an anesthetic, in which at least one simulated blood concentration value of the drug and a concentration value is provided at the site of action of the anesthetic, which, compared to the state of the art, has a markedly increased accuracy compared to the concentration value present in reality.

In the method according to the present invention, the quantity of the drug, especially the quantity per unit of time and thus the rate administered by the drug dosing device is determined, wherein a) the concentration of the drug in the gas exhaled by the patient is measured as a first patient value $c1M$, b) a simulation calculation is carried out, in which a second patient value cp is calculated from the quantity of the drug I administered per unit of time, taking into account a parameter $k10$, c) a simulated first patient value $c1'$ is calculated during the simulation calculation, taking into account the parameter $k10$, d) a comparison of the simulated first patient value $c1'$ to the measured first patient value $c1M$ is carried out, e) an adaptation of the parameter $k10$ on the basis of the comparison is carried out, and f) the calculated second patient value cp is used to generate a control signal S, for example, for the drug dosing device.

Thus, the method according to the present invention is carried out in such a way that a simulation calculation is carried out on the basis of the quantity I of the drug administered to the patient per unit of time and possibly the concentration $c1M$ of this drug in the gas exhaled by the patient, the result of which is the blood concentration of the drug as a second patient value cp. At the same time, a simulated value for the first patient value $c1'$, i.e., the breathing gas concentration of the drug is determined by means of the simulation calculation, and this simulated value is compared to the actually measured value $c1M$. The result of this comparison is used to adapt a parameter used in the simulation calculation.

This parameter may be, for example, a parameter that describes the metabolism of the drug in the patient, and it may especially be the elimination rate $k10$ of the drug from the blood circulation. This parameter describes, even though not alone, the connection between the quantity I of the drug administered by the dosing device per unit of time and the measured concentration c1M thereof in the gas exhaled by the patient as well as the concentration in the blood circulation cp.

Thus, in the method according to the present invention, parameters, which are used for determining the blood concentration of the drug cp, are continuously adapted and thus optimized, so that the accuracy of the simulation is always further improved. Thus, a blood concentration value of the drug cp as a second patient value can in this way be determined with high accuracy, which is then based on, besides other parameters, the actual control and adaptation of the quantity I of the drug administered to the patient per unit of time.

The present invention is not limited to the blood concentration value cp being exclusively based on the control of the drug dosing device, but rather it is also possible that a compartment model is used in the simulation, so that the concentrations in the other compartments may also be included in the determination of the quantity of the drug to be administered per unit of time and thus included in the generation of the control signal.

This simulated blood concentration value cp or this second patient value may especially be compared to a set value cpS, which is preset by an anesthesiologist, and corresponding control signals can be transmitted to the drug dosing device on the basis of this comparison.

The simulation calculation is preferably carried out (with a compartment model used in the simulation) in such a way that:
  the blood circulation forms a first compartment;
  a second and a third compartment are taken into account, for which the concentration of the drug is calculated, wherein it is taken into account that the drug passes at a rate (k12) from the first compartment (V1) into the second compartment (V2) and at a rate (k21) from the second compartment (V2) into the first compartment (V1), and that the drug passes at a rate (k13) from the first compartment (V1) into the third compartment (V3) and at a rate (k31) from the third compartment (V3) into the first compartment (V1);
  the concentration of the drug in the breathing gas forms the first patient value and is calculated, such that a passage of the drug from the first compartment (V1) into the breathing gas takes place at a rate (k10), and the drug is broken down at an elimination rate, which is the parameter (k10), from the first compartment (V1).

A compartment model is used as the basis in such a simulation calculation, which has proven to be advantageous in connection with the calculation of the behavior of the drug concentration over time.

Furthermore, in a preferred embodiment, the passage of the drug from the lung (L) into the breathing gas is calculated by a time delay element of the first order, so that the equation $$\dot{c}1 + k10 \cdot c1 = K \cdot k10 \cdot cp$$

applies to the concentration (c1) of the drug in the breathing gas and its change over time $\dot{c}1$, wherein cp is the concentration of the drug in the blood circulation and K and k10 are constants. This has proven to be a suitable mathematical description of the behavior of the breathing gas concentration over time.

In a preferred embodiment of the method according to the present invention, determination of the quantity I(k) of the drug administered per unit of time, measurement of the first patient value c1M(k), i.e., concentration of the drug in the breathing gas of the patient, a simulation calculation, comparison, adaptation and generation of the control signal take place in a common step (a control step, which is also referred to herein as a control segment), wherein the method proceeds in consecutive steps (consecutive segments) k−1, k, k+1.

In a current step k, a function $f_k$ is applied to a patient status vector x(k−1), which has been determined in a previous step k−1, in the simulation calculation, to determine a simulated patient status vector x'(k) of the current step k. The subscript "k" in the function $f_k$ indicates here that this function describes the connection in discrete time steps (discrete time segments) k, k+1.

It is pointed out in this connection that the term "apply" and the term "function" are not to be considered strictly in the sense of a matrix-vector multiplication, but rather are to be interpreted as broadly, so that the application of a nonlinear function to the status may also be included. In particular, the function and an operator itself may be a function of the patient status, so that nonlinear functions of the patient status shall also be determined from the term function.

The patient status vector x(k) contains the first patient value c1(k), the second patient value cp(k), and the parameter k10(k), which shall be optimized in the course of the method. The simulated patient status vector x'(k) contains the simulated first patient value c1'(k), a simulated second patient value cp'(k), and a simulated parameter k10'(k). Finally, the function $f_k$ of the current step (current segment) k is a function of the parameter k10(k−1), which has been determined in the previous step (previous segment) k−1. Thus, the function $f_k$ is a nonlinear function of the status x(k), since the parameter k10 is also a component of the patient status vector.

The patient status vector x(k) of the current step k is determined from the simulated patient status vector x'(k) of the current step k in such a way that at least the first simulated patient value c1'(k) thereof and the simulated parameter k10'(k) thereof are corrected as a function of the difference between the simulated first patient value c1'(k) and the first patient value c1M(k) measured in the current step.

Thus, in this embodiment, the method is carried out in discrete time steps (discrete time segments), wherein in each time step first a so-called simulated patient status vector x'(k) is generated in such a way that a function $f_k$ is applied to a patient status vector x(k−1), which has been generated in the immediately preceeding step.

It should be pointed out in this connection that the term "patient status vector" is defined in the sense of the present invention by only the scalar quantities mentioned in connection with the respective vector being determined. It is not necessary that these quantities be stored or processed in a connected manner. It is only necessary that all the quantities mentioned in connection with the respective vectors are determined, processed or otherwise treated during the respective time step.

Analogously, it is true for the application of the function to a vector that the scalar quantities contained in the input vector are processed and the scalar quantities mentioned in connection with the output vector are thereby generated. In this case as well, it is not necessary that this processing take place actually in a directly connected manner, but rather it is also conceivable that the individual computing steps necessary in this case proceed entirely separately from one another. In particular, the impression that a software-based implementation of the method according to the present invention must directly depict a mathematical description of an application of an operator to a vector, for example, a matrix-vector multiplication should be avoided.

First, a simulated patient status vector x'(k) is determined by applying a function $f_k$, which describes the development over time of at least of the concentration of the drug in the breathing gas and of the first patient value c1(k) and in the blood and of the second patient value cp(k), to the status vector x(k−1) from the previous step.

This simulated status vector x'(k) is subsequently corrected in such a way that the simulated first patient value c1'(k), i.e., the simulated breathing gas concentration, is compared to the breathing gas concentration c1M(k) measured in the step k currently being carried out. Depending on the difference, the simulated breathing gas concentration c1'(k), the blood concentration cp'(k) and the parameter k10'(k) in question are corrected. After this correction, a new patient status vector x(k) is available for the current step k. In this connection, the parameter k10(k), which describes the breakdown of the drug in the patient and may especially be the elimination rate, at which the drug in question is being broken down, has also been corrected.

An extended Kalman filtering can especially be achieved by means of the above-described preferred embodiment of the method, as will be explained in connection with the preferred exemplary embodiment.

In particular, the generated control signal can be sent to a transfer unit with a display, wherein a value is displayed on the display, which corresponds to the quantity of the drug corresponding to the control signal, which would be generated when forwarding the control signal from the drug dosing device to the patient. However, the control signal is preferably not forwarded directly to the drug dosing device, but rather it requires the intervention of a user such as an anesthesiologist, so that the control signal is sent to the drug dosing device either unchanged or in a changed form for correction of the quantity displayed. For this, either an actuating element at the transfer device can be actuated or the user enters the value on a keyboard or input device at the drug dosing device.

Moreover, the above-mentioned object is accomplished by a drug dosing system with a drug dosing device for administering the drug to a patient, wherein means are provided to determine the quantity of the administered drug and especially the quantity administered per unit of time, with means for determining the concentration of the drug in the breathing gas of the patient, wherein the control system of the drug dosing system is designed to carry out the method explained above.

The present invention is described below based on a drawing showing only one preferred exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
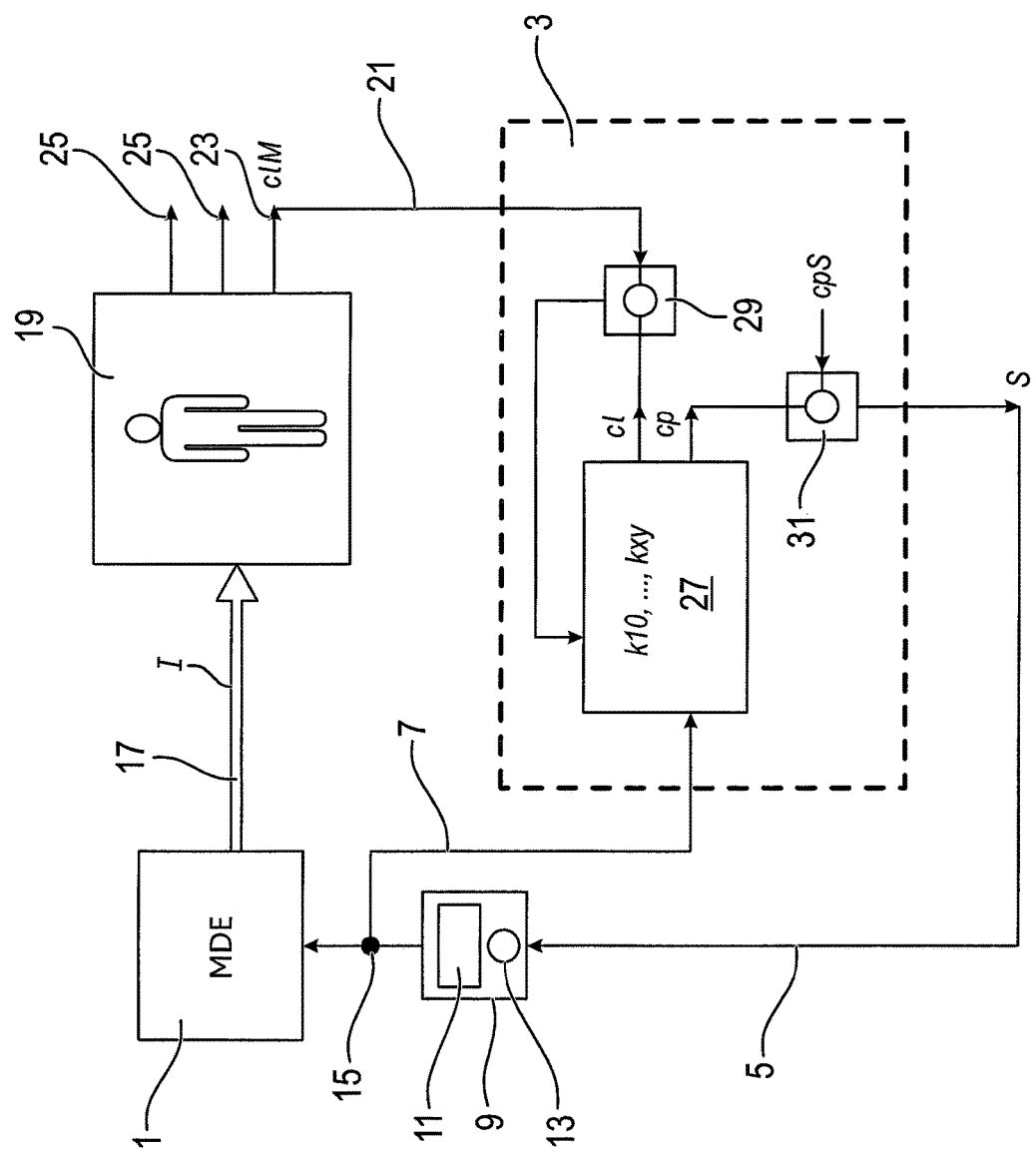
FIG. 1 is a schematic view of the exemplary embodiment of a system according to the present invention for controlling a drug dosing device.

Referring to the drawings, FIG. 1 shows the exemplary embodiment of a drug dosing system according to the present invention, which has a drug dosing device 1 for administering a drug to a patient and a control system 3. The drug may preferably be an anesthetic and especially is propofol, and the drug dosing device 1 may be designed as a conventional syringe pump.

Connections 5, 7 originate from the control system 3, so that the control system 3 can send a control signal S via the connection 5 to a transfer unit 9 described in further detail below. In addition, the control signal S in this exemplary embodiment is returned to the control system 3 via the connection 7.

The transfer unit 9 has a display 11 and at least one actuating element 13. In addition, the transfer unit 9 is connected to the drug dosing device 1 by means of a connection 15. The transfer unit 9 is designed such that, based on the control signal S, which is generated by the control system 3, the value, which indicates the quantity of the drug that is to be administered to the patient 19 per unit of time, is displayed on the display 11 in order to achieve or maintain a set value cpS for the concentration of the drug in the blood circulation. A user such as an anesthesiologist can read the value on the display 11 and make sure that the control signal S is forwarded to the drug dosing device 1 by pressing the actuating element 13, so that the displayed quantity is then actually administered to the patient 19 via the line 17. However, it is also possible that the user changes the value and thus the control signal, for example, by turning the actuating element 13, so that a changed control signal S is then sent to the drug dosing device 1. Thus, it requires the intervention of the user in the system according to the present invention, so that the generated control signal S is transferred and it may also be changed. However, it is also conceivable that the control signal S is transferred directly to the drug dosing device 1 without the intervention of the user. In exactly the same way, it is possible that no connection 15 is present between the transfer unit 9 and the drug dosing device 1, but rather the user manually enters the value displayed on the display 11 on an input device at the drug dosing device 1.

The control signal S transferred by the transfer unit 9 is an indicator of the quantity I of the drug, which is being administered by the drug dosing device 1 to the patient per unit of time, since the control signal S transferred to the drug dosing device 1 forms the reference value for the control of the drug dosing device 1. By returning the control signal S by means of the connection 7, means are obtained here, which determine the quantity I of the drug administered to the patient 19 per unit of time and send it to the control system 3.

In addition, the control system 3 is connected via a further connection 21 to a sensor 23, which is provided at the patient 19 and with which the concentration c1M of the drug administered by the drug dosing device 1 is determined in the gas exhaled by the patient 19.

While the connection 21 is shown here as a direct and wired connection, this connection may be achieved in a wireless manner or via a network like other shown connections as well.

Thus, a signal, which represents this concentration c1M, is transmitted via the connection 21 to the control system 3. In addition, additional sensors 25 may be provided at the patient 19, with which additional patient measured values can be determined and optionally transmitted to the control system 3.

The control system 3 has a computer 27, as well as a comparison unit 29 and a control signal-generating device 31, which are connected to the computer 27.

Figure 2:
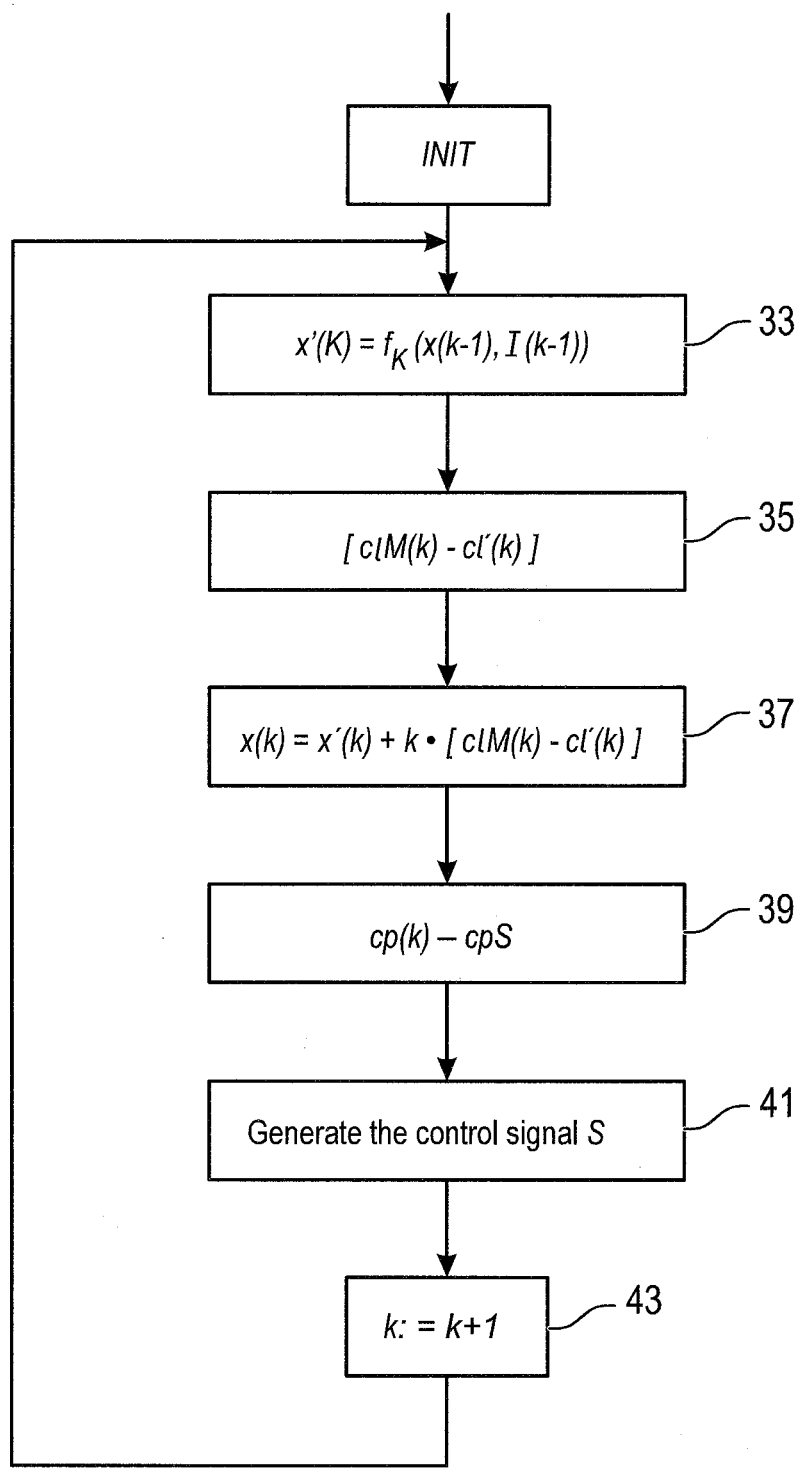
FIG. 2 is a flow chart, which depicts the exemplary embodiment of the method according to the present invention.

The control system 3 now operates as follows, wherein FIG. 2 shows a flow chart, which depicts partial steps (partial control segments) proceeding each in one step (proceeding together in one control segment).

The exemplary embodiment of a control method according to the present invention is explained in connection with a digital computer, a digitally operating comparison unit as well as a digital control signal-generating unit. However, it is entirely conceivable that the method according to the present invention is also achieved by means of analog electronics, so that the present invention shall not be limited to the application or implementation together with digital electronics.

In addition, the units of the control system 3 mentioned above may also be implemented in a single structural unit and not separated from one another.

In the preferred exemplary embodiment of the method according to the present invention described here, a series of partial steps proceed within one step, and these partial steps are repeated in the next step, wherein results which had been calculated in the previous step are used in the next step. Thus, it is a recursive method.

At the beginning of the exemplary embodiment of the method, the computer 27 can first be initialized in an "INIT" step.

Subsequently, a simulated patient status vector x'(k) is calculated by means of the computer 27 in the partial step 33 within the framework of a step k, which can follow a plurality of steps k−1, k−2, . . . already carried out. This takes place in such a way that a function $f_k$ is applied to the patient status vector x(k−1), which had been determined in the previous step (k−1), taking into account the quantity I(k−1) of the drug administered per unit of time and determined in the previous step k−1.

As a first patient value the patient status vector x(k) contains at least the breathing gas concentration c1(k), which the drug that is administered by means of the drug dosing device 1 has in the breathing gas of the patient 19. In addition, the patient status vector x(k) contains a second patient value cp(k), which indicates the concentration of the drug that is being administered by the drug dosing device 1 in the blood circulation of the patient. Finally, the patient status vector x(k) also contains a parameter k10(k), which in this preferred exemplary embodiment describes the breakdown of the drug in the patient and it may especially be the elimination rate in the blood circulation. This parameter is needed in the calculation of the simulated patient status vector x'(k). Analogously, the simulated patient status vector x'(k) determined by applying the function $f_k$ to the patient status vector x(k−1) contains a simulated first patient value and a simulated breathing gas concentration c1'(k), a simulated second patient value and a simulated blood circulation concentration cp'(k) as well as a simulated value k10'(k) for the parameter k10. In this preferred exemplary embodiment, the patient status vector x(k) and the simulated patient status vector x'(k) may thus have the following form:

$$x(k)=(cp(k), \ldots, c1(k), k10(k));$$

$$x'(k)=(cp'(k), \ldots, c1'(k), k10'(k)).$$

This form already suggests that the patient status vector x(k), x'(k) may also contain, in addition to the blood concentration cp, cp', the breathing gas concentration c1, c1' and the elimination rate k10, k10', additional values, which also describe the process of the absorption and breakdown of the drug in the body of a patient. However, this will be explained further below.

When the application of the function $f_k$ to the status vector x(k−1) is shown as a multiplication of both, the function $f_k$ itself also contains the parameter k10(k), as is described in detail below, so that the function $f_k$ is not a linear function of the status vector.

In the then next partial step 35, the difference between the concentration c1M(k) of the drug in the breathing gas measured with the sensor 23 in the current step k and the simulated concentration c1M(k) is determined by means of the comparison unit 29, wherein the measured concentration c1M(k) is transmitted to the comparison unit 29 via the connection 21.

In the now next further partial step 37, the simulated patient status vector x'(k) is corrected, wherein for this an operator K is applied to the difference [c1M(k)−c1'(k)] formed in the comparison unit 29 and the result of this application is added to the simulated patient status vector x'(k). Thus, the new patient status vector x(k) is then obtained.

In the present preferred exemplary embodiment, this new patient status vector x(k) contains, as a second patient value cp(k), the blood concentration of the drug administered by the drug dosing device 1, i.e., propofol, which is otherwise not accessible based on measurement.

This second patient value cp(k) is compared to a set value cpS in the partial step 39 by subtraction by means of the signal-generating device 31, and based on the difference determined, a control signal S is then generated in the partial step 41, which control signal S is transmitted to the transfer unit 9 via the connection 5, so that optionally the quantity I of the drug administered to the patient per unit of time can be adapted. For this, a value is displayed on the display 11 of the transfer unit 9, which corresponds to the quantity of the drug that would be administered to the patient 19 by the drug dosing device, if the control signal S would be forwarded directly to the drug dosing device 1.

A user may press the actuating element 13 of the transfer unit 9 in order to transfer the control signal S unchanged to the drug dosing device 1. However, it is also possible that the user turns the actuating element 13 to change the control signal S and thus the administered quantity of the drug.

Finally, the signal, which represents the quantity I that is administered by the drug dosing device, is returned to the control system and the computer 27 by means of the line 7.

However, besides the concentration cp(k) of the drug in the blood circulation, additional patient values may also be included in the generation of the control signal S in partial step 41, as will be explained below. Thus, the generation of the control signal S is not determined alone by the determination of the difference between the blood concentration cp and the corresponding set value cpS set by a physician.

Subsequently, the passage to the next full step takes place, in which the subscript k is increased by 1 in the partial step 43. A return to partial step 33 takes place, and the partial steps 33 through 43 are passed through again.

In the present preferred exemplary embodiment, an extended Kalman filtering algorithm is carried out by the above-described way of proceeding and suitable selection of the operation K.

In principle, in an extended Kalman filtering algorithm first a so-called prediction is stated in a first step in order to describe a current status x(k) of any system by a function or an operator $f_k$ being applied to a vector x(k−1) describing a previous status in order to obtain a simulated status vector x'(k), wherein besides the previous status x(k−1), an input quantity u(k−1) affecting the status and a noise component w(k−1) are also included. Thus, $$x'(k)=f_k(x(k-1),u(k-1),w(k-1)).$$

The function or the operator $f_k$ describes the behavior over time of the system, which is described by the status vectors x(k), x(k−1), wherein the function $f_k$ is not a linear function of the status vector x(k−1), but rather it is a nonlinear function. Subsequently, the simulated status vector x'(k) is corrected in such a way as to obtain the new status vector x(k) that the simulated status vector x'(k) is compared by subtraction generally to a function G of a vector xM(k), which contains measured values describing the status of the system in question. A function K of this comparison result is added to the simulated status vector x'(k) in order to then obtain the new status vector x(k), so that $$x(k)=x'(k)+K(k)\times[xM(k)-G\times x'(k)].$$

Reference is made to the corresponding technical literature for detailed information on extended Kalman filtering.

For the selection of the status vectors as well as the function and the operator $f_k$ the above-described exemplary embodiment is based on the following considerations.

Figure 3:
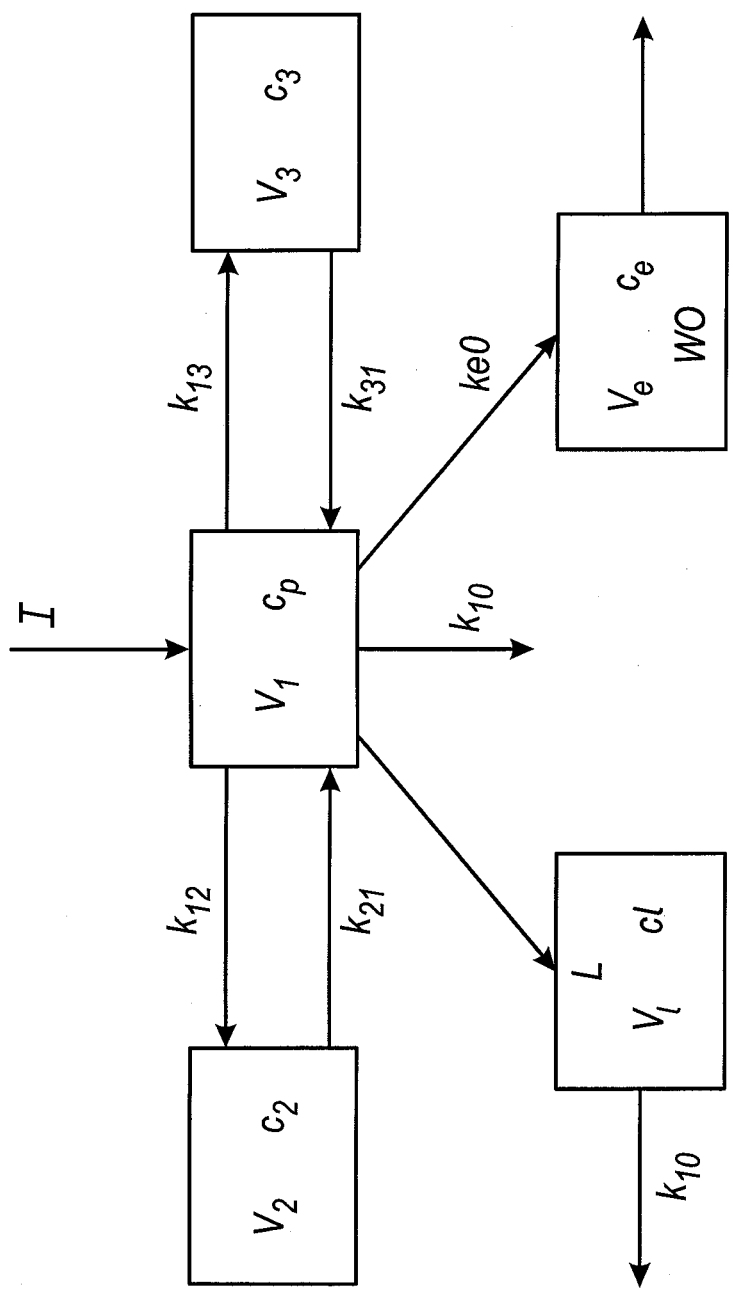
FIG. 3 is a schematic view of a model on which the exemplary embodiment of the method according to the present invention is based.

The absorption, redistribution, breakdown and release to the breathing gas of an intravenously administered drug such as propofol is described for the preferred exemplary embodiment shown here on the basis of a modified three-compartment model shown schematically in FIG. 3.

For this, it is assumed that a quantity I of the drug absorbed per unit of time in the blood circulation (V1)—forming the first compartment—occurs at different rates k12, k13 into a second and a third compartment V2, V3. The second compartment V2 represents the muscles, while the third compartment V3 is formed by fatty tissue and connective tissue. This splitting into a second and a third compartment V2, V3 takes place because, for example, propofol is deposited for different lengths of time in the fatty tissue and connective tissue and in the muscles, so that especially the rates k21 and k31, at which propofol again returns into the blood circulation and the first compartment V1, differ sharply.

In addition, the drug or propofol is broken down at an elimination rate k10 from the blood circulation V1, and it passes at a rate k11 into the lung (L) and from there at a rate k10 into the breathing gas, wherein it is assumed here that the concentration in the breathing gas c1 develops according to a time delay element of the first order compared to the concentration cp of the drug in the blood circulation and this does not contribute to the breakdown of the drug. This means that the equation or differential equation $$\dot{c}1+k10\cdot c1=K\cdot K10\cdot cp$$

applies to the concentration c1 of the drug in the breathing gas and its change over time $\dot{c}1$, wherein K is a proportionality constant.

Finally, the concentration of the drug in the blood circulation is a defined action that is symbolized by the site of action WO, wherein the extent of the action occurs at a rate ke0 depending on the concentration in the blood circulation cp. For the case of propofol as the drug, this means that the depth of anesthesia is linked with the blood concentration cp over the rate ke0.

With these assumptions, a differential equation system can be set up, with which the course over time of the concentration cp, c2, and c3 of the drug or of propofol in the three compartments V1, V2 and V3 as well as the concentration c1 in the lung and the extent of the action ce at the site of action WO is described. The patient status vector then has the form $$x(t) = \begin{bmatrix} c_p(t) \\ c_2(t) \\ c_3(t) \\ c_e(t) \\ c_l(t) \\ k_{10}(t) \end{bmatrix},$$

and the following differential equation system is obtained:

$$\dot{x}(t) =$$

$$f(x(t), I(t)) = \begin{bmatrix} (-k_{10}(t) - k_{12} - k_{13})c_p(t) + k_{12}c_2(t) + k_{13}c_3(t) + \frac{1}{V_1}I(t) \\ k_{21}c_p(t) - k_{21}c_2(t) \\ k_{31}c_p(t) - k_{31}c_3(t) \\ k_{e0}c_p(t) - k_{e0}c_e(t) \\ K\cdot k_{10}\cdot c_p(t) - k_{10}\cdot c_l(t) \\ 0 \end{bmatrix}$$

In this case, the parameter k10, which describes the elimination of the drug or of propofol from the blood circulation, is itself variable over time.

The function $f_k$ for the above-described method shown in FIG. 2 can be generated from this differential equation system, wherein this method proceeds in discrete steps k.

$$x(k) = f_k(x(k-1), I(k-1)) =$$

$$\begin{bmatrix} (1 - dT(k_{10}(k-1) + k_{12} + k_{13}))c_p(k-1) + dTk_{12}c_2(k-1) + dTk_{13}c_3(k-1) + dT\frac{1}{V_1}I(k-1) \\ dTk_{21}c_p(k-1) + (1 - dTk_{21})c_2(k-1) \\ dTk_{31}c_p(k-1) + (1 - dTk_{31})c_3(k-1) \\ dTk_{e0}c_p(k-1) + (1 - dTk_{e0})c_e(k-1) \\ dT\cdot K\cdot k_{10}\cdot c_p(k-1) + (1 - dT\cdot k_{10})c_l(k-1) \\ k_{10}(k-1) \end{bmatrix}$$

Thus, the parameter k10 is part of the status vector x(k) and due to the fact that a correction of the simulated patient status vector x'(k) takes place in partial step 37 in order to determine the patient status vector x(k), not only is the simulated second patient value cp'(k) corrected, but also the parameter k'10(k), which is itself needed for the calculation of the blood concentration or of the second patient value cp'(k). The correction takes place here according to the equation $$x(k)=x'(k)+K(k)\times[c1M(k)-c1'(k)],$$

wherein the function K(k) is obtained in a known manner from covariance matrices. This correction leads to the parameter k10 being optimized during the repeated passing through the partial steps 33 through 43, wherein the optimization takes place by a comparison of the simulated first patient value c1'(k), i.e., the breathing gas concentration, to the measured breathing gas concentration c1M(k).

Thus, in the method according to the present invention, besides the second patient value cp(k) that is actually beneficial for the control of the drug dosing device 1, a first patient value c1(k), which can be obtained by measurement, is also determined, so that the quality of the simulation calculation can be optimized by a comparison of this first patient value to the measured patient value.

This is of very great advantage in the present case especially because the parameter k10(k), which describes the elimination of a drug such as propofol from the blood circulation of the patient, varies very greatly from patient to patient, even if the external data of the patients, such as height and body weight are essentially in agreement.

As can be seen, moreover, not only the first and the second patient values, i.e., the concentration of the drug in the breathing gas c1(k) and in the blood circulation cp(k), but also the concentration c2, c3 of the drug in the second and third compartments V2, V3 as well as the concentration ce at the site of action WO (see FIG. 3), are calculated with the simulation calculation. These concentrations may be taken into account in the generation of the control signal S in partial step 41. In particular, the fact that a certain quantity, as suggested by the rates K21 and K31 in FIG. 3, returns from the second and third compartments V2, V3 back into the blood circulation VI may be included in the determination of the quantity I of the drug to be sent to the drug dosing device 1, so that the quantity I to be administered can be reduced and thus the control signal S can be adapted correspondingly.

All in all, the method according to the present invention enables the control system 3 to provide a blood concentration value cp of the drug in a markedly more accurate manner than in the state of the art, which can then be used for the further control of the dosing device 1. In this case, it may remain open in which way the course over time of the blood concentration of the respective drug and especially of an anesthetic is adjusted. In the present case, it is only of interest how the current value of the drug in the blood of the patient, on which value this later control is based, is determined.

While specific embodiments of the invention have been shown and described in detail to illustrate the application of the principles of the invention, it will be understood that the invention may be embodied otherwise without departing from such principles.

APPENDIX

List of Reference Numbers

1 Drug dosing device
3 Control system
5 Connection
7 Connection
9 Transfer unit
11 Display
13 Actuating element
15 Connection
17 Line
19 Patient
21 Connection
23 Sensor
25 Sensors
27 Computer
29 Comparison unit
31 Control signal-generating device
33 Partial step
35 Partial step
37 Partial step
39 Partial step
41 Partial step
43 Partial step

What is claimed is:

1. A method for controlling a drug dosing device for administering a drug to a patient, the method comprising:
   determining a quantity of the drug administered to the patient from the drug dosing device via a drug quantity determination device;
   measuring a concentration of the drug in the gas exhaled by the patient as a first patient value via a concentration determining device;
   providing a control system configured for:
      carrying out a simulation calculation, in which a second patient value is calculated from the administered quantity of the drug, taking into account a parameter;
      calculating a simulated first patient value in the simulation calculation, taking into account the parameter;
      comparing the simulated first patient value to the measured first patient value;
      adapting the parameter on the basis of the comparison; and
      generating a control signal based on the second patient value, wherein the drug dosing device adapts the quantity of the drug administered to the patient based on the control signal, wherein the simulation calculation comprises a compartment model carried out based on:
   blood circulation forming a first compartment;
   a second compartment being taken into account, for which a concentration of the drug is calculated;
   a third compartment being taken into account, for which a concentration of the drug is calculated;
   the drug passing from the first compartment into the second compartment at a first rate;
   the drug passing from the second compartment into the first compartment at a second rate;
   the drug passing from the first compartment into the third compartment at a third rate;
   the drug passing from the third compartment into the first compartment at a fourth rate;
   the concentration of the drug in the breathing gas forming the first patient value being calculated such that a passage of the drug from the first compartment into the breathing gas takes place at a breathing gas rate; and
   the drug being broken down from the first compartment at an elimination rate, which is the parameter, wherein the simulation calculation is carried out such that a passage of the drug from the lung into the breathing gas is calculated by a time lag element of the first order, so that an equation:

$$\dot{c}1 + k10 \cdot c1 = K \cdot k10 \cdot cp \qquad (5)$$

applies to the concentration (c1) of the drug in the breathing gas and a change to the concentration over time ($\dot{c}1$), wherein cp is the concentration of the drug in the blood circulation and K and k10 are constants.

2. A method in accordance with claim 1, wherein the second patient value is a concentration of the drug in the blood circulation of the patient.

3. A method in accordance with claim 2, wherein the calculated second patient value is compared to a set value for the second patient value and the control signal is generated based on the comparison of the second patient value to the set value.

4. A method in accordance with claim 1, wherein the calculated second patient value is compared to a set value for the second patient value and the control signal is generated based on the comparison of the second patient value to the set value.

5. A method in accordance with claim 1, wherein the determination of the administered quantity of the drug, the measurement of the first patient value, the simulation calculation, the comparison, the adaptation and the generation of the control signal together form a control step, wherein:
the method proceeds in consecutive steps;
for a current step in the simulation calculation, a function is applied to a patient status vector, which status vector is determined in a previous step, to determine a simulated patient status vector of the current step;
the patient status vector contains the first patient value, the second patient value and the parameter;
the simulated patient status vector contains the simulated first patient value, a simulated second patient value and a simulated parameter;
the function of the current step is a function of the parameter, which parameter is determined in a previous step;
the patient status vector of the current step is determined from the simulated patient status vector of the current step, such that at least the first simulated patient value and the simulated parameter are corrected as a function of a difference between the simulated first patient value and the first patient value measured in the current step.

6. A method in accordance with claim 1, wherein:
the drug quantity determination device comprises a display;
a value is displayed on the display, which value corresponds to a quantity of the drug corresponding to the control signal.

7. A method for controlling a drug dosing device for administering a drug to a patient, the method comprising:
determining a quantity of the drug administered to the patient from the drug dosing device via a drug quantity determination device;
measuring a concentration of the drug in the gas exhaled by the patient as a first patient value via a concentration determining device;
providing a control system configured for:
carrying out a simulation calculation, in which a second patient value is calculated from the administered quantity of the drug, taking into account a parameter;
calculating a simulated first patient value in the simulation calculation, taking into account the parameter;
comparing the simulated first patient value to the measured first patient value;
adapting the parameter on the basis of the comparison; and
generating a control signal based on the second patient value, wherein the drug dosing device adapts the quantity of the drug administered to the patient based on the control signal, wherein the simulation calculation comprises a compartment model carried out based on:
blood circulation forming a first compartment;
a second compartment being taken into account, for which a concentration of the drug is calculated;
a third compartment being taken into account, for which a concentration of the drug is calculated;
the drug passing from the first compartment into the second compartment at a first rate;
the drug passing from the second compartment into the first compartment at a second rate;
the drug passing from the first compartment into the third compartment at a third rate;
the drug passing from the third compartment into the first compartment at a fourth rate;
the concentration of the drug in the breathing gas forming the first patient value being calculated such that a passage of the drug from the first compartment into the breathing gas takes place at a breathing gas rate; and
the drug being broken down from the first compartment at an elimination rate, which is the parameter.

8. A drug dosing system for administering a drug to a patient, the drug dosing system comprising:
a drug dosing device for administering the drug to the patient, the drug dosing device comprising a drug quantity determination device to determine a quantity of the administered drug;
a concentration determining device to determine a quantity of the drug in the breathing gas of the patient; and
a control system configured such that:
a concentration of the drug in the gas exhaled by the patient is measured as a first patient value;
a simulation calculation is carried out, in which a second patient value is calculated from the administered quantity of the drug and the first patient value based on a parameter;
a simulated first patient value is calculated in the simulation calculation, taking into account the parameter;
a comparison of the simulated first patient value to the measured first patient value is carried out;
an adaptation of the parameter is carried out on the basis of the comparison; and
the calculated second patient value is used to generate a control signal, wherein the drug dosing device adapts the quantity of the administered drug based on the control signal, the second patient value being a concentration of the drug in the blood circulation of the patient, wherein the simulation calculation is carried out based on:
blood circulation forming a first compartment;
a second compartment being taken into account, for which a concentration of the drug is calculated;
a third compartment being taken into account, for which a concentration of the drug is calculated;
the drug passing from the first compartment into the second compartment at a first rate;
the drug passing from the second compartment into the first compartment at a second rate;

the drug passing from the first compartment into the third compartment at a third rate;
the drug passing from the third compartment into the first compartment at a fourth rate;
the concentration of the drug in the breathing gas forming the first patient value is calculated such that a passage of the drug from the first compartment into the breathing gas takes place at a breathing gas rate; and
the drug is broken down from the first compartment at an elimination rate, which is the parameter, wherein the simulation calculation is carried out such that a passage of the drug from the lung into the breathing gas is calculated by a time lag element of the first order, so that an equation:

$$\dot{c}1 + k10 \cdot c1 = K \cdot k10 \cdot cp$$

applies to the concentration (c1) of the drug in the breathing gas and a change to the concentration over time ($\dot{c}1$), wherein cp is the concentration of the drug in the blood circulation and K and k10 are constants.

9. A system in accordance with claim 8, wherein the calculated second patient value is compared to a set value for the second patient value and the control signal is generated.

10. A system in accordance with claim 9, wherein:
the drug quantity determination device comprises a display;
the control signal is sent to the transfer unit; and
a value is displayed on the display, which value corresponds to a quantity of the drug corresponding to the control signal.

11. A system in accordance with claim 8, wherein:
the drug quantity determination device comprises a display;
the control signal is sent to the drug quantity determination device; and
a value is displayed on the display, which value corresponds to a quantity of the drug corresponding to the control signal.

12. A system in accordance with claim 8, wherein the calculated second patient value is compared to a set value for the second patient value and the control signal is generated based on the comparison of the second patient value to the set value.

13. A system in accordance with claim 8, wherein the determination of the administered quantity of the drug, the measurement of the first patient value, the simulation calculation, the comparison, the adaptation and the generation of the control signal together form a control segment, wherein:
the control system is configured to proceed in consecutive control segments;
for a current control segment in the simulation calculation, a function is applied to a patient status vector, which status vector is determined in a previous control segment, to determine a simulated patient status vector of the current control segment;
the patient status vector contains the first patient value, the second patient value and the parameter;
the simulated patient status vector contains the simulated first patient value, a simulated second patient value and a simulated parameter;
the function of the current control segment is a function of the parameter, which parameter is determined in a previous control segment;
the patient status vector of the current control segment is determined from the simulated patient status vector of the current control segment, such that at least the first simulated patient value and the simulated parameter are corrected as a function of a difference between the simulated first patient value and the first patient value measured in the current control segment.

14. A system in accordance with claim 8, wherein:
the drug quantity determination device comprises a display;
a value is displayed on the display, which value corresponds to a quantity of the drug corresponding to the control signal.

15. A method for controlling a drug dosing device for administering a drug to a patient, the method comprising:
determining a quantity of the drug administered to the patient from the drug dosing device via a drug quantity determination device;
measuring a concentration of the drug in the gas exhaled by the patient as a first patient value via a concentration determining device;
providing a control system configured for:
carrying out a simulation calculation, in which a second patient value is calculated from the administered quantity of the drug, taking into account a parameter;
calculating a simulated first patient value in the simulation calculation, taking into account the parameter;
comparing the simulated first patient value to the measured first patient value;
adapting the parameter on the basis of the comparison; and
generating a control signal based on the second patient value, wherein the drug dosing device adapts the quantity of the drug administered to the patient based on the control signal, wherein the determination of the administered quantity of the drug, the measurement of the first patient value, the simulation calculation, the comparison, the adaptation and the generation of the control signal together form a control step, wherein:
the method proceeds in consecutive steps;
for a current step in the simulation calculation, a function is applied to a patient status vector, which status vector is determined in a previous step, to determine a simulated patient status vector of the current step;
the patient status vector contains the first patient value, the second patient value and the parameter;
the simulated patient status vector contains the simulated first patient value, a simulated second patient value and a simulated parameter;
the function of the current step is a function of the parameter, which parameter is determined in a previous step;
the patient status vector of the current step is determined from the simulated patient status vector of the current step, such that at least the first simulated patient value and the simulated parameter are corrected as a function of a difference between the simulated first patient value and the first patient value measured in the current step.

16. A drug dosing system for administering a drug to a patient, the drug dosing system comprising:
a drug dosing device for administering the drug to the patient, the drug dosing device comprising a drug quantity determination device to determine a quantity of the administered drug;
a concentration determining device to determine a quantity of the drug in the breathing gas of the patient; and
a control system configured such that:
a concentration of the drug in the gas exhaled by the patient is measured as a first patient value;

a simulation calculation is carried out, in which a second patient value is calculated from the administered quantity of the drug and the first patient value based on a parameter;
a simulated first patient value is calculated in the simulation calculation, taking into account the parameter;
a comparison of the simulated first patient value to the measured first patient value is carried out;
an adaptation of the parameter is carried out on the basis of the comparison; and
the calculated second patient value is used to generate a control signal, wherein the drug dosing device adapts the quantity of the administered drug based on the control signal, wherein the determination of the administered quantity of the drug, the measurement of the first patient value, the simulation calculation, the comparison, the adaptation and the generation of the control signal together form a control segment, wherein:
the control system is configured to proceed in consecutive control segments;
for a current control segment in the simulation calculation, a function is applied to a patient status vector, which status vector is determined in a previous control segment, to determine a simulated patient status vector of the current control segment;
the patient status vector contains the first patient value, the second patient value and the parameter;
the simulated patient status vector contains the simulated first patient value, a simulated second patient value and a simulated parameter;
the function of the current control segment is a function of the parameter, which parameter is determined in a previous control segment;
the patient status vector of the current control segment is determined from the simulated patient status vector of the current control segment, such that at least the first simulated patient value and the simulated parameter are corrected as a function of a difference between the simulated first patient value and the first patient value measured in the current control segment.

* * * * *